US010470701B2

(12) United States Patent
Balloni et al.

(10) Patent No.: US 10,470,701 B2
(45) Date of Patent: Nov. 12, 2019

(54) MONITORING SYSTEMS AND METHODS FOR MONITORING A CONDITION OF A PATIENT

(71) Applicant: General Electric Company, Schenectady, NY (US)

(72) Inventors: William James Balloni, Menomonee Falls, WI (US); Jamon Lewis, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 580 days.

(21) Appl. No.: 14/870,782

(22) Filed: Sep. 30, 2015

(65) Prior Publication Data
US 2017/0086733 A1  Mar. 30, 2017

(51) Int. Cl.
*A61B 5/02* (2006.01)
*A61B 5/00* (2006.01)
(Continued)

(52) U.S. Cl.
CPC .......... *A61B 5/4821* (2013.01); *A61B 5/044* (2013.01); *A61B 5/0452* (2013.01);
(Continued)

(58) Field of Classification Search
CPC .............................. A61B 5/044; A61B 5/0452
See application file for complete search history.

(56) References Cited

U.S. PATENT DOCUMENTS 6,765,983 B2 * 7/2004 Yan ................. A61B 6/032
  378/8
7,054,679 B2 * 5/2006 Hirsh ................ A61B 5/02028
  600/483

(Continued)

FOREIGN PATENT DOCUMENTS

WO  2011017778 A1  2/2011
WO  2014152719 A1  9/2014

OTHER PUBLICATIONS

International Search Report for corresponding PCT application PCT/US2016/052079, dated Dec. 28, 2016; 10 pages.
(Continued)

*Primary Examiner* — Michael J D Abreu
(74) *Attorney, Agent, or Firm* — Dean D. Small; The Small Patent Law Group, LLC

(57) ABSTRACT

Monitoring system configured to provide a health chart on an operator display. The health chart includes a plurality of indicators that identify patient parameters. The plurality of indicators form a column that extends parallel to a first axis. The health chart also includes linear projections that are aligned with respective indicators and extend parallel to a second axis that is perpendicular to the first axis. The linear projections represent values of the patient parameters that correspond to the respective indicators. The values are determined by the physiological data obtained from corresponding sensors. The patient monitoring system is configured to determine lengths of the linear projections based on the physiological data. The lengths extend from proximal
(Continued)

ends of the linear projections to distal ends of the linear projections. The distal ends move parallel to the second axis toward or away from the respective indicators to change the length.

17 Claims, 7 Drawing Sheets

(51) Int. Cl.
| | | |
|---|---|---|
| A61B 5/0452 | (2006.01) | |
| G16H 10/60 | (2018.01) | |
| A61B 5/044 | (2006.01) | |
| A61B 5/021 | (2006.01) | |
| A61B 5/04 | (2006.01) | |
| A61B 5/0402 | (2006.01) | |
| A61B 5/0476 | (2006.01) | |
| A61B 5/01 | (2006.01) | |
| A61B 5/08 | (2006.01) | |

(52) U.S. Cl.
CPC .......... *A61B 5/7425* (2013.01); *A61B 5/7445* (2013.01); *G16H 10/60* (2018.01); *A61B 5/01* (2013.01); *A61B 5/021* (2013.01); *A61B 5/0402* (2013.01); *A61B 5/04012* (2013.01); *A61B 5/0476* (2013.01); *A61B 5/0816* (2013.01)

(56) References Cited

U.S. PATENT DOCUMENTS

| | | | |
|---|---|---|---|
| 7,774,052 | B2 | 8/2010 | Burton et al. |
| 7,881,778 | B2 | 2/2011 | Rantala |
| 8,515,531 | B2 | 8/2013 | Costa Ribalta et al. |
| 8,583,222 | B2 | 11/2013 | Nelwan et al. |
| 8,688,207 | B2 * | 4/2014 | Rajagopalan ........ A61B 5/0452 600/523 |
| 2004/0082840 | A1 | 4/2004 | Chen |
| 2004/0193064 | A1 * | 9/2004 | Shusterman ........ A61B 5/0452 600/504 |
| 2005/0182333 | A1 | 8/2005 | Nagata et al. |
| 2010/0024950 | A1 | 2/2010 | Broos et al. |
| 2011/0184692 | A1 | 7/2011 | Andersen |
| 2012/0001920 | A1 | 1/2012 | Halpern et al. |
| 2012/0041328 | A1 | 2/2012 | Rajagopalan et al. |
| 2012/0323133 | A1 | 12/2012 | Lindauer et al. |
| 2015/0011902 | A1 | 1/2015 | Wang |
| 2015/0097701 | A1 | 4/2015 | Al-Ali et al. |

OTHER PUBLICATIONS

Sangachand et al.; Continuous ST-segment monitoring: nurses' attitudes, practices and qualily of patient care; Decision Support, Evidence Series; 2013 (2 pages).
Using ST Map to shorten response time and improve efficiency; Decision Support, Evidence Series; 2010 (2 pages).
Martin et al.; An Interactive Tool for the Evaluation of ECG Visualisation Formats; Computing in Cardiology 2013; 40: 779-782.
Steg et al.; ESC Guidelines forht emanagement of acute myocardial infarction in patients presenting with ST-segment elevation; European Heart Journal; Sep. 11, 2012; 51 pages.
Sandau et al.;Continuous ST-Segment Monitoring: Protocol for Practice; American Association of Critical-Care Nurses; vol. 29, No. 4; Aug. 2009; pp. 39-51.
Drew et al.; Practice Standards for Electrocardiographic Monitoring in Hospital Settings; American Heart Association, Inc. Oct. 26, 2004; 30 pages.
Bruhn et al.; Depth of Anaesthesia monitoring: what's available, what's validated and what's next?; British Journal of Anaesthesia 97 (1): 2006; pp. 85-94.
Bond et al.; A usability evaluation of medical software at an expert conference setting; Computer Methods and Programs in Biomedicine 113, 2014; pp. 383-395.
Sangkachand et al.; Continuous ST-Segment Monitoring: Nurses' Attitudes, Practices, and Quality of Patient Care; American Journal of Critical Care; May 2011; vol. 20, No. 3; 14 pages.
Musizza et al.; Monitoring the Depth of Anaesthesia; Sensors, 2010, 10 Pages 10896-10935.

\* cited by examiner

MONITORING SYSTEMS AND METHODS FOR MONITORING A CONDITION OF A PATIENT

BACKGROUND

The subject matter herein relates generally to patient monitoring systems and methods, and more particularly, to patient monitoring systems and methods that monitor multiple parameters to facilitate identifying alarm conditions.

Patient monitoring systems are configured to receive physiological data from a patient, analyze the physiological data, and communicate information to a healthcare provider so that the healthcare provider may assess a condition of the patient. Monitoring systems may include one or more sensors that detect the physiological data and an operator display that presents the information to the healthcare provider. The information includes recognizable physiological parameters that the healthcare provider may use to determine a health status or condition of the patient. Non-limiting examples of these parameters include heart rate, blood pressure, electrocardiographic (ECG) data, auditory evoked potentials, and electroencephalogram (EEG) data. ECG data, in particular, may be used to diagnose certain cardiac conditions, such as complex arrhythmias, myocardial ischemia, and prolonged QT intervals. EEG data may be used to assess a patient's depth of sedation (or depth of anesthesia). Diagnosing the above conditions often includes simultaneously analyzing multiple parameters. This diagnosis is made more difficult because the values that may be considered problematic depend upon the patient.

Monitoring systems are often particularly configured for monitoring certain conditions. For example, monitoring systems exist for detecting ECG data and analyzing the ST-segments from the ECG data. Changes in ST-segments may indicate myocardial ischemia in which blood flow to the patient's heart is reduced. Traditional ST-segment monitoring systems present a table to the healthcare provider. For example, the healthcare provider may be presented with a table having eleven values that can be positive or negative and are updated in real-time. Although these ST-segment monitoring systems provide useful information for assessing a patient's health, it is often difficult to interpret the information quickly. Because they can be difficult or frustrating to use, some healthcare providers decide not to use the systems.

Another, more recent, ST-segment monitoring system displays two multi-axis portraits or maps of the ST-segment data. In each portrait, six axes intersect one another at a center of the portrait and each axis intersects a perimeter of the portrait. The ends of the axes, which are positioned along the perimeter of the portrait, correspond to the placement of the electrodes used to obtain the ECG data from the patient. While monitoring a patient, colored sections are shown on the portrait that indicate areas of the heart that are ischemic. Again, although this ST-segment monitoring system provides useful information for assessing a patient's status, the portraits are not intuitive and it is often difficult to interpret the information quickly and/or correctly. A substantial amount of education may be necessary so that the healthcare provider will feel comfortable using the system.

BRIEF DESCRIPTION

In an embodiment, a monitoring system configured to monitor a condition of a patient is provided. The monitoring system includes a plurality of sensors that are configured to operably couple to a patient to detect physiological data from the patient. The patient monitoring system also includes an operator display that is configured to present a monitoring window that includes viewable information that is based on the physiological data of the patient. The patient monitoring system also includes a processor that is configured to execute programmed instructions stored in memory. The processor, when executing the programmed instructions, performs the following operations. The processor receives the physiological data from the patient and provides a health chart in the monitoring window that includes a plurality of indicators that identify corresponding patient parameters. The plurality of indicators form a column that extends parallel to a first axis. The health chart also includes linear projections that are aligned with respective indicators and extend parallel to a second axis that is perpendicular to the first axis. The linear projections represent values of the patient parameters that correspond to the respective indicators. The values are determined by the physiological data obtained from corresponding sensors. The processor determines corresponding lengths of the linear projections based on the physiological data. The corresponding lengths extend from proximal ends of the linear projections to distal ends of the linear projections. The distal ends move parallel to the second axis to change the length of the corresponding linear projection.

Optionally, the lengths of the linear projections may be scaled relative to a maximum length if the patient parameter is less than a designated threshold. Upon one of the patient parameters obtaining the designated threshold, the lengths of the other linear projections may be scaled relative to the value of the patient parameter that obtained the designated threshold.

In certain aspects, the indicators and corresponding linear projections form a plurality of groups in which each group includes multiple indicators and the corresponding linear projections. Each group is visually differentiated from at least one other group. Optionally, at least two of the groups correspond to different anatomical regions of the heart. Optionally, during an alarm event, the linear projections of a first group extend designated distances away from the corresponding indicators in a first direction and the linear projections of a second group extend designated distances away from the corresponding indicators in a second direction that is opposite the first direction.

In an embodiment, a method is provided that includes receiving physiological data from a patient and determining values for a plurality of patient parameters. The values are a function of the physiological data. The method also includes displaying a health chart on an operator display. The health chart includes a plurality of indicators that identify corresponding patient parameters. The plurality of indicators form a column in the health chart that extends parallel to a first axis. The health chart also includes linear projections that are aligned with respective indicators and extend parallel to a second axis that is perpendicular to the first axis. The method also includes determining corresponding lengths of the linear projections. The lengths of the linear projections represent the values of the patient parameters that correspond to the respective indicators. The corresponding lengths extend from proximal ends of the linear projections to distal ends of the linear projections. The distal ends move parallel to the second axis toward or away from the respective indicators to change the length of the corresponding linear projection.

In an embodiment, a monitoring system configured to monitor a condition of a patient is provided. The monitoring system includes a plurality of electrodes configured to couple to a patient to detect electrocardiographic (ECG) data of the patient. The monitoring system also includes an operator display that is configured to present a monitoring window to a user. The monitoring window includes viewable information that is based on the ECG data. The monitoring system also includes a processor configured to execute programmed instructions stored in memory. The processor, when executing the programmed instructions, performs the following operations. The processor receives the ECG data from the patient and provides a health chart in the monitoring window that includes a plurality of indicators that identify corresponding ECG leads. The plurality of indicators form a column that extends parallel to a first axis. The health chart also includes linear projections that are aligned with respective indicators and extend parallel to a second axis that is perpendicular to the first axis. The linear projections represent ST-segment deviations of the ECG leads that are determined by the ECG data obtained from the corresponding electrodes. The processor also determines corresponding lengths of the linear projections based on the ST-segment deviations. The corresponding lengths extend from proximal ends of the linear projections to distal ends of the linear projections. The distal ends move parallel to the second axis to change the length of the corresponding linear projection.

DETAILED DESCRIPTION

Figure 1:
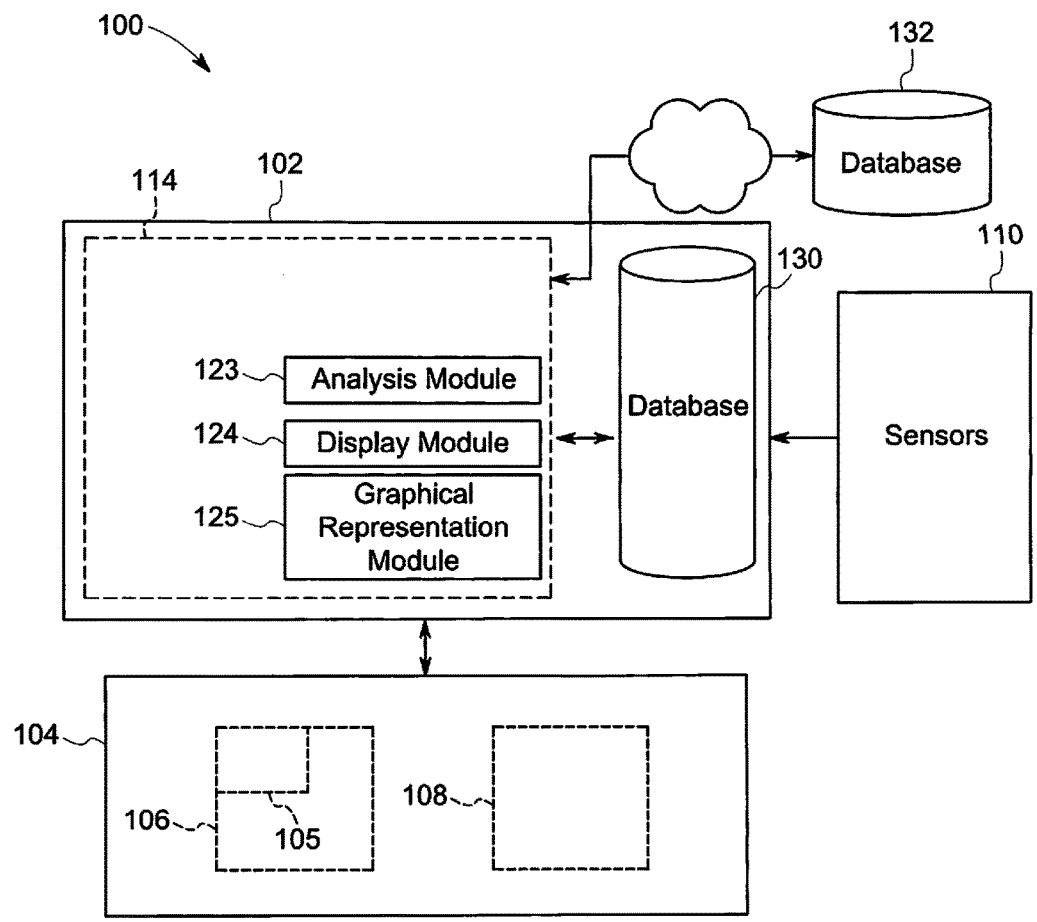
FIG. 1 is a block diagram of an exemplary system for displaying waveform information in accordance with one embodiment.

Exemplary embodiments that are described in detail below provide systems and methods that analyze physiological data that may be used to diagnose a patient of a particular condition. Although the various embodiments may be described in connection with electrocardiography, the systems and methods described herein are not limited to electrocardiographic (ECG) analysis. Non-limiting examples of other types of analysis that embodiments may be used in connection with include cardiotocographic analysis, electroencephalographic (EEG) analysis, electromyographic analysis, depth of sedation, among others. Embodiments may be used for more than one type of analysis (e.g., ECG and depth of sedation). Physiological information displayed by embodiments described herein may relate to, for example, electrical activity, blood pressure, heart rate, body temperature, respiratory rate, depth of sedation score, or intrauterine pressure.

At least one technical effect of various embodiments includes providing a health chart that shows magnitudes of certain values in a manner that may enable a healthcare provider to determine a condition of the patient more quickly than known monitoring systems.

As used herein, an element or step recited in the singular and proceeded with the word "a" or "an" should be understood as not excluding plural of said elements or steps, unless such exclusion is explicitly stated. For example, the phrase "a processor" may include a single processor, a multi-core processor, or a plurality of processors. If a plurality of processors are used, the plurality of processors may be found within a single unit (e.g., computer) or may be distributed throughout a system, such as in multiple units. If one processor is used, the claims may recite the processor as "only a single processor."

Furthermore, references to "one embodiment" are not intended to be interpreted as excluding the existence of additional embodiments that also incorporate the recited features. Moreover, unless explicitly stated to the contrary, embodiments that "comprise," "have," or "include" an element or a plurality of elements that have a particular property may also include additional such elements that do not have that particular property. Furthermore, when a feature is described as being based on a parameter or being a function of a parameter, the term "based on" or "function of" should not be interpreted as the parameter being the sole parameter or primary parameter, but may include the possibility that the element is also based on other parameters.

As used herein, the term "physiological signals" may include only one type of signals or multiple types of signals. For examples, physiological signals may include physiological signals relating to a first type (e.g., ECG signals) and physiological signals relating to a second type (e.g., EEG signals, heart rate, pulse oximetry, etc.).

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. For example, one or more of the functional blocks (e.g., modules, processors, or memories) may be implemented in a single piece of hardware (e.g., a general purpose signal processor or random access memory, hard disk, or the like). Similarly, programs may be stand alone programs, may be incorporated as subroutines in an operating system, may be functions in an installed software package, may be a software surface package that is run from a computer server remotely, and the like. It should be understood that the various embodiments are not limited to the arrangements and instrumentality shown in the drawings.

FIG. 1 is a block diagram of an exemplary monitoring system 100 that is configured to monitor a condition of a patient. The monitoring system 100 includes a computing device or system 102 that is communicatively coupled to a user interface 104. The user interface 104 may include instruments (e.g., user display), hardware, and software (or a combination thereof) that permit the system 100 to display information to the user and, in some embodiments, permit the user to provide user inputs or selections. The user may be a healthcare provider, such as a doctor, nurse, or other suitably qualified individual. The user interface 104 may include an operator display 106 (e.g., monitor, screen, touchscreen, and the like) and an input device 108 (e.g., keyboard, computer mouse, tracking button, touchscreen, and the like) that is capable of receiving and communicating user inputs to the computing system 102. In some embodiments, a device constituting the input device 108 may also be the device constituting the operator display 106 (e.g., touchscreen). The operator display 106 may be configured to show a viewable area that includes a monitoring window having a health chart 105, which is described in greater detail below. The user interface 104 may also be configured to query or prompt the user of the system 100 for designated information.

The monitoring system 100 may be integrated into one component (e.g., a laptop computer) or may be several components that may or may not be located near each other. The monitoring system 100 may include sensors 110 that are configured to detect physiological data, such as from an individual (e.g., a patient), and communicate the physiological data to the computing system 102. In particular embodiments, the sensors 110 are electrodes configured to detect electrical activity within the patient, such as the electrical activity of the heart and/or brain. Alternatively or in addition to electrical activity, the sensors 110 may be configured to detect other physiological data, such as a heart rate, body temperature, blood pressure, respiratory rate, intrauterine pressure, etc.

In particular embodiments, the monitoring system 100 detects, analyzes, and displays data relating to ECG and/or EEG. Accordingly, the monitoring system 100 may detect electrical activity of the heart over a period of time using electrodes placed on a patient's body (e.g., chest, limbs, head). The electrodes detect the electrical changes on the skin that arise from the heart muscle depolarizing during each heartbeat or, alternatively, from current in the neurons of the brain. In a conventional 12-lead ECG, ten electrodes are placed on the patient's limbs and on the surface of the chest. The overall magnitude of the heart's electrical potential is then measured from twelve different angles ("leads") and is recorded over a period of time. As such, an overall magnitude and direction of the electrical depolarization may be captured throughout multiple cardiac cycles.

The computing system 102 may include or be part of a server system, a workstation, a desktop computer, a laptop computer, or a personal device, such as a tablet computer or a smartphone. However, the above are only examples and the computing system 102 may be other types of systems or devices. In the illustrated embodiment, the computing system 102 includes a system controller 114, which may comprise a controller, processor, or other logic-based device. The system controller 114 may have or be communicatively coupled to modules for performing methods as described herein. The modules may include an analysis module 123, a display module 124, and a graphical representation module 125. Each of the modules 123-125 may be a part of another module or include another module. For example, the graphical representation module 125 may be a part of the display module 124. In addition to the above, there may be several other modules or sub-modules of the system controller 114 that are not shown. Each of the modules 123-125 may be communicatively coupled to a memory or database 130 and/or communicatively coupled to a remote memory or database 132 via, for example, the internet or other communication network. Although the database 130 is shown as being shared by the modules 123-125, each module 123-125 may have a separate memory or database.

The analysis module 123 is configured to receive the physiological signals from the sensors 110 and analyze the physiological signals. In some embodiments, the physiological signals from one sensor 110 may represent a patient parameter. For example, the physiological signals from a pulse oximeter may directly correspond to an oxygen level in the blood. In other embodiments, a patient parameter may be based on the physiological signals from two or more sensors. For example, values of at least some ECG leads may be based on the physiological signals of two or more electrodes. Accordingly, the analysis module 123 may also process the physiological signals from one or more sensors 110 to determine corresponding patient parameters. In some embodiments, the analysis module 123 may also analyze the physiological signals and/or the patient parameters to identify events-of-interest. For example, the analysis module 123 may analyze the patient parameters to determine when an alarm condition, such as an ischemic event, has occurred. The analysis module 123 may use one or more algorithms to identify the events-of-interest. If an event-of-interest is identified, the analysis module 123 may communicate this information to the display module 124 and/or the graphical representation module 125 to notify the user.

The display module 124 may operate in conjunction with the analysis module 123 and/or the graphical representation module 125. For example, the graphical representation module 125 may store graphical objects that represent patient parameters, such as the indicators described below. The display module and/or the graphical representation module 125 may generate graphics that correspond to the data provided by the analysis module 123. For example, the display module and/or the graphical representation module 125 may generate a linear projection having a length that is based on the data provided by the analysis module 123. The data and corresponding lengths may be re-calculated throughout a monitoring session to give the appearance of real-time monitoring. In such embodiments, the data and corresponding lengths may be re-calculated every ten seconds, every five seconds, every three seconds, every one second, or more frequently. Alternative embodiments may re-calculate the data and corresponding lengths every twenty second, thirty seconds, or more. The graphical representation module 125 may also be configured to store various graphical objects that provide the overall appearance of a health chart.

The databases 130 and 132 may store data that can be retrieved by the components or modules of the system 100 and other remotely located systems through the internet or other communication network. The databases 130 and 132 can store data that the modules 123-125 require in order to accomplish the functions of the modules 123-125. For example, the databases 130 and 132 can store the physiological signals obtained from the sensors 110.

The modules 123-125 (and the system controller 114) include one or more processors, microprocessors, controllers, microcontrollers, or other logic based devices that operate based on instructions stored on a tangible and non-transitory computer readable storage medium. For example, the modules 123-125 may be embodied in one or more processors that operate based on hardwired instructions or software applications. The databases 130 and 132 can be or include electrically erasable programmable read only memory (EEPROM), simple read only memory (ROM), programmable read only memory (PROM), erasable programmable read only memory (EPROM), FLASH memory, a hard drive, or other type of computer memory.

As used herein, the terms "computer" or "computing system" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer" or "computing system."

The computer or processor executes a set of instructions that are stored in one or more storage elements, in order to process input data and provide output data in the form of a health chart, among other things. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes described herein. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine. The program is compiled to run on designated operating systems.

Figure 2:
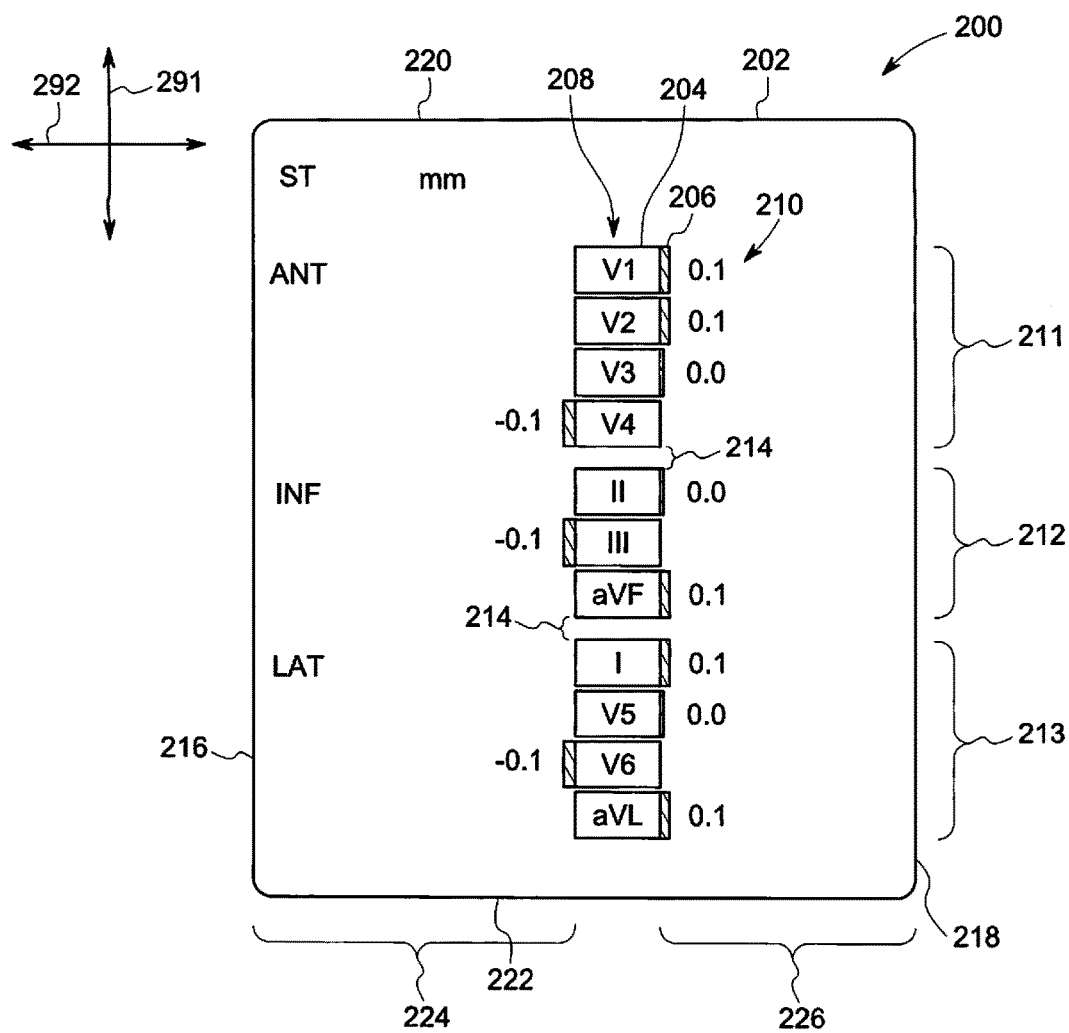
FIG. 2 illustrates a health chart that may be presented to a user of the system of FIG. 1. The health chart in FIG. 2 includes information about a patient during a steady state or baseline condition.

FIG. 2 illustrates an exemplary monitoring window 200 in accordance with an embodiment. The monitoring window 200 is configured to be presented on an operator display, such as the operator display 106 (FIG. 1). The monitoring window 200 may span an entirety of a viewable area along the operator display. In other embodiments, however, the monitoring window 200 may only span a portion of the viewable area. The monitoring window 200 is oriented with respect to first and second axes 291, 292. The first axis 291 may also be referred to as a vertical axis of the monitoring window 200, and the second axis 292 may also be referred to as a horizontal axis of the monitoring window 200.

The monitoring window 200 includes a health chart 202 having information that may be used by the user (e.g., healthcare provider) to monitor and assess a condition of the patient. In an exemplary embodiment, the condition is a cardiac condition. For example, the user may be able to determine whether the patient is suffering a cardiac event, such as myocardial ischemia. However, embodiments may be configured to present information for determining other cardiac conditions or other conditions of a patient. For example, embodiments may be configured to present information for determining a depth of sedation or depth of anesthesia. In FIG. 2, the health chart 202 is displaying information that indicates the patient has a baseline condition (e.g., a non-alarming or non-concerning condition).

The information presented to the user includes a plurality of indicators 204 and a plurality of linear projections 206. Optionally, numerical values 210 may also be displayed. The indicators 204 represent or identify patient parameters that are being monitored by the patient monitoring system. Each of the linear projections 206 is aligned with a respective indicator 204 and, optionally, a respective numerical value 210. The linear projection 206 visually represents the numerical value of the patient parameter relative to a reference value. The numerical value 210 identifies the actual value. Accordingly, in the illustrated embodiment, each patient parameter is represented by a single indicator 204, a single linear projection 206, and a single numerical value 210 at a single moment or period in time. It is contemplated, however, that a patient parameter may be represented by more than one indicator 204, more than one linear projection 206, and/or more than one numerical value 210 in other embodiments. For example, blood pressure may be represented by both a diastolic value and a systolic value. In such instances, a linear projection may be generated for each of the diastolic and systolic values.

By way of example, the indicator 204 labeled "V1" corresponds to a patient parameter, the ECG lead V1, which is often monitored in 12-lead ECG data. A linear projection 206 is aligned with the V1 indicator 204. (The linear projection 206 for the lead V1 is more visible in FIG. 3.) In this case, the linear projection 206 is laterally aligned with the V1 indicator 204. The linear projection 206 that is aligned with the V1 indicator 204 is aligned with a numerical value 210 of "0.1," which is also aligned with the V1 indicator 204. As described in greater detail below, the linear projection 206 may have a length that correlates to the absolute value of the respective numerical value 210. The length may also be based on other factors in some embodiments.

As shown, the patient parameters represented by the indicators 204 include the leads from 12-lead ECG data. The leads are derived from ten electrodes positioned on the patient. More specifically, the patient parameters include the six chest leads that detect the depolarization wave in the frontal plane. These may also be referred to as the precordial leads and are V1, V2, V3, V4, V5, and V6. Each of the chest leads corresponds to an electrode that has a designated position on the patient's chest. The patient parameters also include extremity leads I, II, III, aVL, and aVF. Optionally, the extremity lead aVR (not shown) may be displayed. The extremity leads are derived from electrodes that are positioned on the left and right arm and left and right legs.

Although the patient parameters correspond to patient parameters that are detected by 12-lead ECG data, it should be understood that other embodiments may display patient parameters that are based on other physiological data and that may be used in assessing a patient's health status. For example, the patient parameters may correspond to data that is used to determine a depth of sedation. The patient parameters may include those found in EEG data.

In the illustrated embodiment, each of the indicators 204 includes a block-shaped graphical object with symbols (e.g., text) within the object. Each of the objects of the indicators 204 has the same size and shape as other objects. The symbols may identify the patient parameter. In other embodiments, the indicators 204 may only include symbols. For instance, the indicators 204 may only include text that identifies the patient parameter.

The indicators 204 are arranged in a column 208 that extends parallel to the first axis 291. The indicators 204 are stacked substantially side-by-side and aligned with one another to form the column 208. The column 208 is spaced apart from edges of the health chart 202 such that open spaces exist on either side of the column 208. More specifically, the health chart 202 includes first edges 216, 218 that extend parallel to each other and the first axis 291, and second edges 220, 222 that extend parallel to each other and the second axis 292. The distance between the first edges 216, 218 represents a width of the health chart 202, and the distance between the second edges 220, 222 represents a height of the health chart 202.

As shown, open spaces 224, 226 exist along opposite sides of the column 208. In the illustrated embodiment, the open space 224 is positioned between the first edge 216 and the column 208, and the open space 226 is positioned between the first edge 218 and the column 208. The open spaces 224, 226 may extend along the first axis 291 for an entire height or length of the column 208. The open spaces 224, 226 are configured to allow the linear projections 206 to lengthen into the open spaces 224, 226. In some embodiments, the open spaces 224, 226 are configured relative to a maximum length of the linear projections 206. The linear projections 206 are capable of extending away from the corresponding indicator 204 in a direction that is parallel to the second axis 292. In the illustrated embodiment, the linear projections 206 may extend in either direction (e.g., one or the other, not both). However, it is contemplated that two linear projections may simultaneously extend away from a common indicator 204 in other embodiments.

As shown, the indicators 204 and the linear projections 206 form a plurality of groups 211, 212, 213 in which each group includes a multiple indicators 204 and the linear projections 206 that correspond to the indicators 204 of the group. In particular embodiment, the groups 211-213 are visually differentiated from one another. More specifically, the appearance of the groups 211-213 informs the user or gives the impression that the patient parameters of one group are more associated with one another or grouped closer to one another than the patient parameters of other groups. For example, in the illustrated embodiment, adjacent groups are separated from one another by a spacing 214. The spacing 214 between the indicators 204 of different groups is greater than a spacing between adjacent indicators 204 within the same group. As shown, the indicators 204 of the group 211 substantially abut each other. For example, the indicators 204 may touch each other or have a nominal gap therebetween. The spacing 214 is greater than the nominal gap. In other embodiments, the distance between adjacent indicators 204 may be greater than shown in FIG. 2, but the spacing 214 may be greater than this other distance. In FIG. 2, the spacing 214 may also exist between adjacent linear projections 206 of different groups.

It should be understood, however, that the indicators 204 and/or linear projections 206 of one group may be visually differentiated with the respective elements of the other groups in different manners. For example, the indicators 204 of one group may have a common color, size, and/or font that is different from the color, size, or font, respectively, of the indicators 204 of the adjacent group. As another example, the linear projections 206 of one group may have a common width, color, and/or shape that is different from the width, color, or shape, respectively, of the linear projections 206 of the adjacent group. Alternatively or in addition to the above, adjacent groups may be separated by a boundary line that extends between the adjacent indicators 204 of the different groups and/or the linear projections 206 of the different groups. For example, each group may be surrounded by an outline (e.g., rectangular box) that visually informs the viewer that the indicators 204 within the box are associated with each other in some manner.

The indicators 204 or, more specifically, the patient parameters that the indicators 204 represent may be associated with one another in a predetermined manner. For example, in the illustrated embodiment, the indicators 204 of the patient parameters are arranged by regions of the heart. The group 211 corresponds to anterior walls, the group 212 corresponds to inferior walls, and the group 213 corresponds to lateral walls. As such, the groups 211, 212, and 213 are labeled "ANT," "INF," and "LAT," respectively. However, as described above, the groups 211, 212, and 213 may be visually differentiated in other manners. In such embodiments, the indicators 204 may display relationships between individual ST segment measurement deviations such that localized conditions within the heart can be discerned. In particular, the indicators 204 are arranged to facilitate identifying the onset of an anterior ST segment elevation myocardial infarction (or anterior STEMI).

Accordingly, the patient parameters may be arranged in the health chart 202 according to anatomical regions. It should be understood, however, that other types of arrangements may be used. For example, as demonstrated with respect to FIGS. 3 and 4, embodiments may also arrange the patient parameters by positive or negative correlations during designated events. More specifically, as demonstrated below, each of the indicators 204 of group 211 will have a positive value and each of the indicators 204 of the group 212 will have a negative value during anterior STEMI.

In some embodiments, during an alarm event (such as anterior STEMI), the linear projections 206 of the group 211 extend designated distances away from the corresponding indicators 204 in a first direction. The linear projections 206 of the group 212 extend designated distances away from the corresponding indicators 204 in a second direction that is opposite the first direction. The first and second directions are opposite directions that extend parallel to the second axis 292.

In determining whether an event-of-interest is occurring, it may be necessary to make a number of different decisions or to consider separate factors. In other words, a diagnosis may require consideration of different sub-events. Accordingly, the patient parameters in the health chart 202 may be arranged to facilitate determining these sub-events. For example, anterior STEMI may be readily identified when the patient parameters of the anterior walls have substantially increased values and when the patient parameters of the inferior walls have substantially decreased values. In this example, a first sub-event (or sub-condition) is the patient parameters of the anterior walls having substantially increased values. In FIG. 2, the patient parameters for determining this sub-event are grouped together. The second sub-event (or sub-condition) is the patient parameters of the inferior walls having substantially decreased values. In FIG. 2, the patient parameters for determining this sub-event are grouped together. As such, the user may more readily identify when anterior STEMI is occurring because the patient parameters for analyzing the first sub-event are grouped together and the patient parameters for analyzing the second sub-event are grouped together. Moreover, the two groups are positioned adjacent to each other so both sub-events may be recognized substantially simultaneously.

Figure 3:
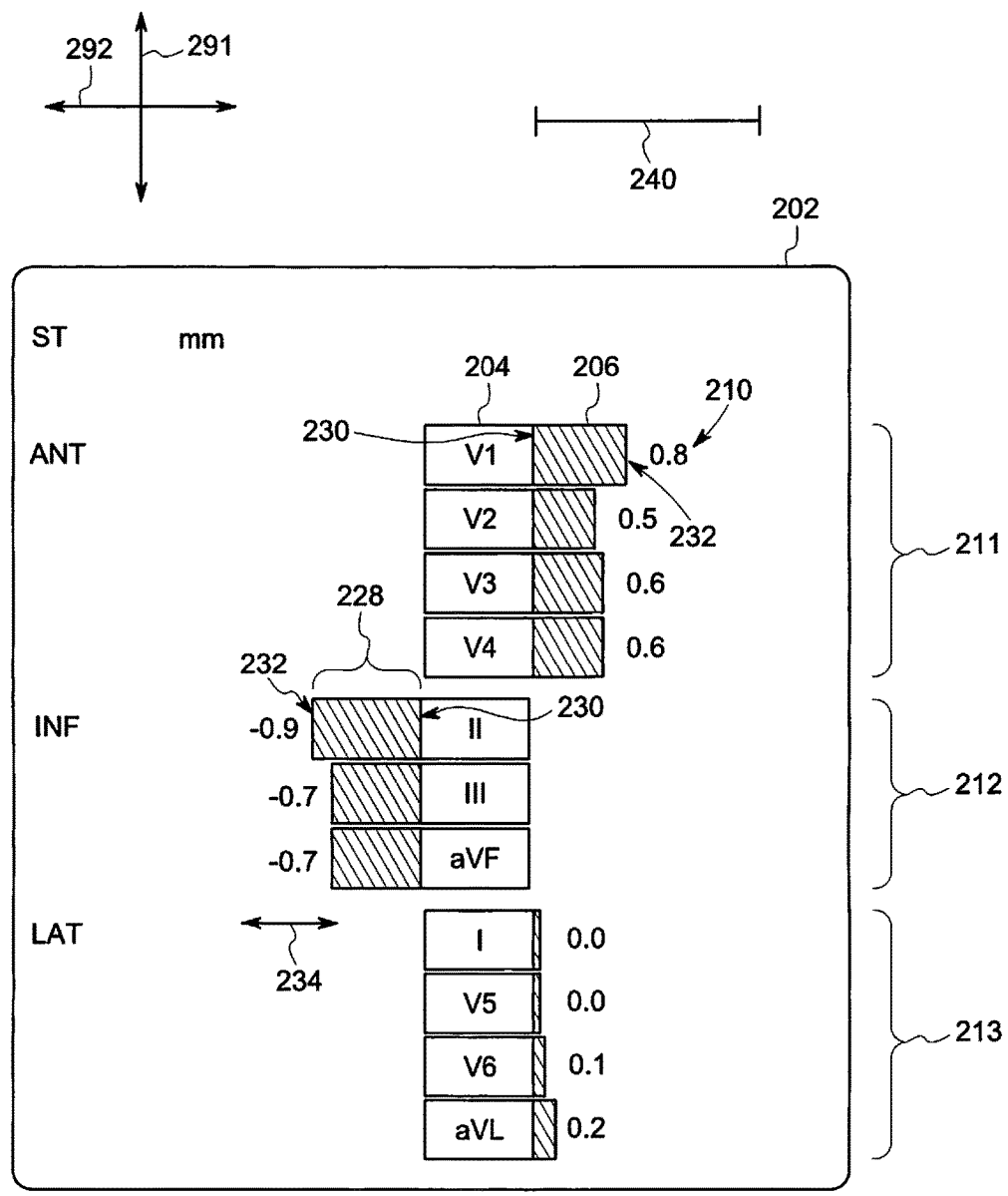
FIG. 3 illustrates the health chart of FIG. 2 when the patient is progressing toward an alarm condition.

FIG. 3 illustrates the health chart 202 when the information indicates that the patient is progressing toward an alarm condition (e.g., myocardial ischemia). In FIG. 3, however, the patient has not yet triggered an alarm and is in a pre-alarm condition (or condition that warrants more concern than a baseline condition). As shown, the numerical values 210 of the groups 211, 212 have changed. The numerical values 210 of the group 211 have increased substantially (e.g., become more positive), and the numerical values 210 of the group 211 have decreased substantially (e.g., become more negative). Accordingly, lengths 228 of the linear projections 206 for the groups 211, 212 have substantially increased as compared to the lengths in FIG. 2.

Each of the linear projections 206 has a proximal end 230 and a distal end 232. The length 228 of the corresponding linear projection 206 extends between the corresponding proximal and distal ends 230, 232. In the illustrated embodiment, each proximal end 230 is positioned adjacent to the indicator 204 that the corresponding linear projection 206 is associated with. Each distal end 232 is positioned away from the indicator 204 that the corresponding linear projection 206 is associated with. In one or more embodiments, the proximal end 230 is positioned closer to the indicator 204 than the distal end 232. In alternative embodiments, however, one or more of the distal ends 232 may be positioned closer to the corresponding indicator 204.

In the illustrated embodiment, the distal end 232 is configured to move parallel to the second axis 292 (as indicated by the bi-directional arrow 234) to change the length 228 of the corresponding linear projection 206. In the illustrated embodiment, the distal end 232 moves toward or away from the respective indicators 204. The amount of movement (and the length 228 of the corresponding linear projection 206) is based on re-calculated numerical values 210.

In the illustrated embodiment, the lateral position (e.g., position relative to the second axis 292) of the numerical values 210 is a function of the numerical value 210. In some embodiments, the numerical value 210 may have a fixed position relative to the distal end 232. As such, the numerical value 210 may give the appearance of being tethered to the distal end 232 of the corresponding linear projection 206. In other embodiments, however, the numerical value 210 may not have a fixed position relative to the corresponding distal end 232. For example, the numerical values 210 may be aligned to form a column (not shown). The numerical values may have the same position within the column throughout the monitoring session.

Embodiments set forth herein may color code at least one of the linear projections 206, the indicators 204, or the numerical values 210 based on the value of the corresponding patient parameter. For example, if the value of the patient parameter is under a designated baseline threshold, the linear projection 206, the indicator 204, and/or the numerical value 210 may be colored in green. If the value of the patient parameter passes a designated baseline threshold but is less than an alarm threshold, the linear projection 206, the indicator 204, and/or the numerical value 210 may be colored in orange. If the value of the patient parameter passes the baseline threshold and the alarm threshold, the linear projection 206, the indicator 204, and/or the numerical value 210 may be colored in red or yellow. It should be understood that other colors may be used to represent baseline conditions, pre-alarm conditions, and alarm conditions. Alternatively or in addition to the above, the linear projections 206, the indicators 204, and/or the numerical values 210 may flash or the patient monitoring system may give an audible sound. In other embodiments, the linear projections 206, the indicators 204, and/or the numerical values 210 of a corresponding group may indicate a pre-alarm or alarm condition if only one of the patient parameters of the groups satisfies a designated condition or a plurality of the patient parameters satisfy designated conditions.

The thresholds or designated conditions may be values of the patient parameters. The threshold may be a common value (whether negative or positive) for one or more of the patient parameters. For example, the pre-alarm threshold may be 0.5 and the alarm threshold may be 2.0. In this case, the alarm threshold may be +2.0 for the patient parameters of the groups 211, 213, and the alarm threshold may be −2.0 for the patient parameters of the group 212. In other embodiments, however, the thresholds for the different patient parameters may be different. For example, the alarm threshold for V1 may be 2.0, but the alarm threshold for III may be −1.5. In some embodiments, the system enables the user to select the threshold value. For example, the system may receive user inputs that designated the threshold values.

As described above, the lengths 228 of the linear projections 206 are a function, at least in part, of the values of the patient parameters that the linear projections 206 correspond to. For example, in FIG. 3, each of the linear projections 206 has a length 228 that is scaled relative to a maximum length 240, which is shown off of the health chart 202 for illustrative purposes. The maximum length 240 may or may not be presented to the user in the health chart 202.

In an exemplary embodiment, the maximum length 240 occurs when the value of the patient parameter is 2.0, which corresponds to 2.0 mm in an ECG graph. Thus, if the value of the patient parameter is less than the designated threshold, the length 228 is based on the ratio of the value to the designated threshold. As one example, if the maximum length 240 is 4 cm on the health chart 202 and the value of the patient parameter is 0.5, then the length 228 is 0.5/2.0 or 0.25 of the maximum length 240. In this example, the length 228 when the value is 0.5 is 1 cm (0.25*4 cm).

In FIG. 3, each of the lengths 228 is proportional to the ratio between the value of the corresponding parameter and the designated threshold, which is 2.0. More specifically, each of the lengths 228 is a designated percentage of the maximum length 240. Table 1 lists the absolute percentages for the example shown in FIG. 3. When the absolute percentage is 0%, the linear projections may have a nominal length. It is noted that each of the values in Table 1 is less than the designated threshold. As described with respect to FIG. 4 and Table 2, in some embodiments, the lengths 228 of the linear projections 206 may also be a function of another value when the designated threshold is exceeded.

TABLE 1

| Group | ST Label | Value | Formula | Percentage (Absolute) |
| --- | --- | --- | --- | --- |
| Anterior | V1 | 0.8 | ((100/2.0) * 0.8) | 40% |
|  | V2 | 0.5 | ((100/2.0) * 0.5) | 25% |
|  | V3 | 0.6 | ((100/2.0) * 0.6) | 30% |
|  | V4 | 0.5 | ((100/2.0) * 0.6) | 30% |
| Inferior | II | −0.9 | ((100/2.0) * −0.9) | 45% |
|  | III | −0.7 | ((100/2.0) * −0.7) | 35% |
|  | avF | −0.7 | ((100/2.0) * −0.7) | 35% |
| Lateral | I | 0.0 | ((100/2.0) * 0.0) | 0% |
|  | V5 | 0.0 | ((100/2.0) * 0.0) | 0% |
|  | V6 | 0.1 | ((100/2.0) * 0.1) | 5% |
|  | aVL | 0.2 | ((100/2.0) * 0.2) | 10% |

Figure 4:
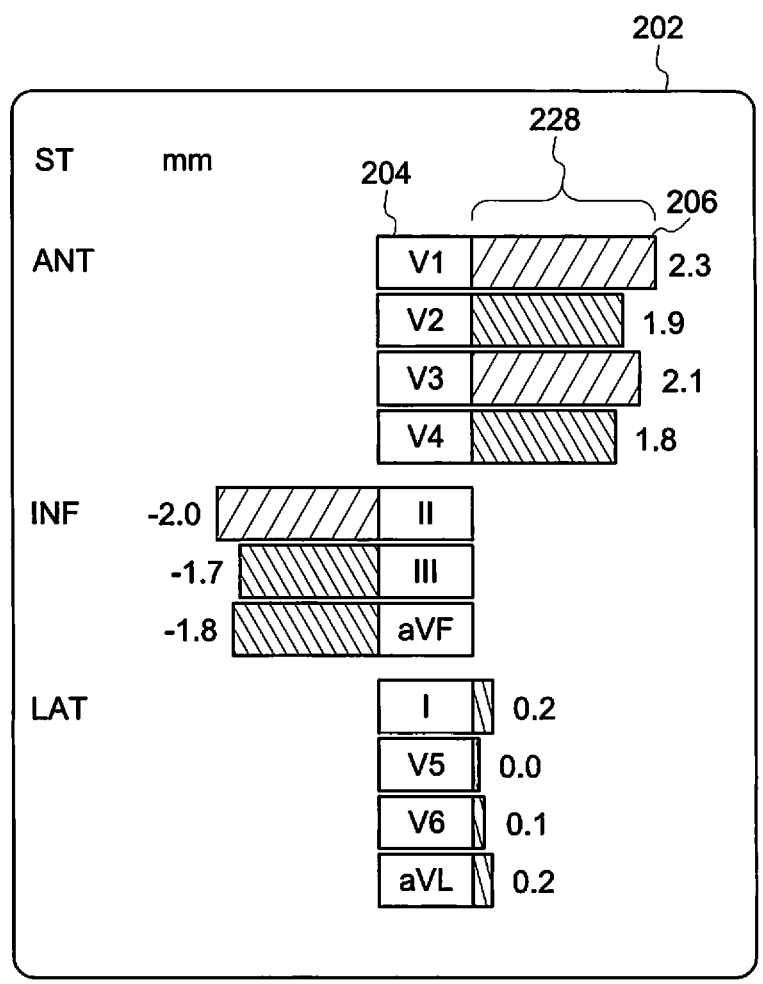
FIG. 4 illustrates the health chart of FIG. 2 when the patient is in an alarm condition.

FIG. 4 illustrates the health chart 202 when the information indicates that the physiological data of the patient has triggered an alarm condition. For example, the V1 and V3 indicators 204 have exceeded an alarm threshold of 2.0. The II indicator 204 has reached the alarm threshold of −2.0. In some embodiments, when the value of a patient parameter is equal to or exceeds an alarm threshold, the linear projections 206 may have a different color. For example, the V1, V3, and III indicators 204 may be colored red as indicated by different cross-sectional hatching. In FIG. 4, the I, V5, V6, and aVL indicators 204 have not passed the pre-alarm threshold and are colored in green. The V2, V4, III, and aVF indicators 204 have exceeded the pre-alarm threshold but have not exceeded the alarm threshold. Accordingly, the V2, V4, III, and aVF indicators 204 are colored in orange as indicated by different cross-sectional hatching. Although the above describes particular colors when certain conditions occur, it should be understood that a variety of colors may be used.

In some embodiments, the lengths 228 of the linear projections 206 may also be a function of another value among the patient parameters. For example, the lengths 228 may be scaled relative to the greatest value of the patient parameters that has also achieved or passed a designated threshold. As shown in FIG. 4, each of the V1, V3, and II indicators 204 has passed or achieved the designated threshold. Among these patient parameters, the patient parameter of V1 is the greatest magnitude (e.g., 2.3). Thus, in the illustrated embodiment, the lengths 228 of the other linear projections 206 are scaled relative to the value of the patient parameter V1. Table 2 is provided below and provides the lengths of the other patient parameters relative to the length of the patient parameter V1.

TABLE 2

| Group | ST Label | Value | Formula | Percentage (absolute) |
|---|---|---|---|---|
| Anterior | V1 | 2.3 | ((100/2.3) * 2.3) | 100% |
| | V2 | 1.9 | ((100/2.3) * 1.9) | 82.6% |
| | V3 | 2.1 | ((100/2.3) * 2.1) | 91.3% |
| | V4 | 1.8 | ((100/2.3) * 1.8) | 78.2% |
| Inferior | II | −2.0 | ((100/2.3) * −2.0) | 86.9% |
| | III | −1.7 | ((100/2.3) * −1.7) | 73.9% |
| | avF | −1.8 | ((100/2.3) * −1.8) | 78.2% |
| Lateral | I | 0.2 | ((100/2.3) * 0.2) | 8.6% |
| | V5 | 0.0 | ((100/2.3) * 0.0) | 0% |
| | V6 | 0.1 | ((100/2.3) * 0.1) | 4.3% |
| | aVL | 0.2 | ((100/2.3) * 0.2) | 8.6% |

Accordingly, in some embodiments, the lengths 228 of the linear projections 206 are scaled relative to a maximum length. However, when the value of one of the linear projections 206 obtains the designated threshold, the lengths 228 of the other linear projections 206 are scaled relative to the value of patient parameter (or the length of the linear projection) that obtained the designated threshold.

The above example scales each of the lengths of all of the patient parameters relative to the value of one of the patient parameters. In other embodiments, the lengths of the patient parameters in one group may be scaled relative to the maximum value in the group, if that maximum value has exceeded the designated threshold. If the group does not have a value that exceeds the designated threshold, then the lengths may be scaled relative to the maximum length.

Figure 5:
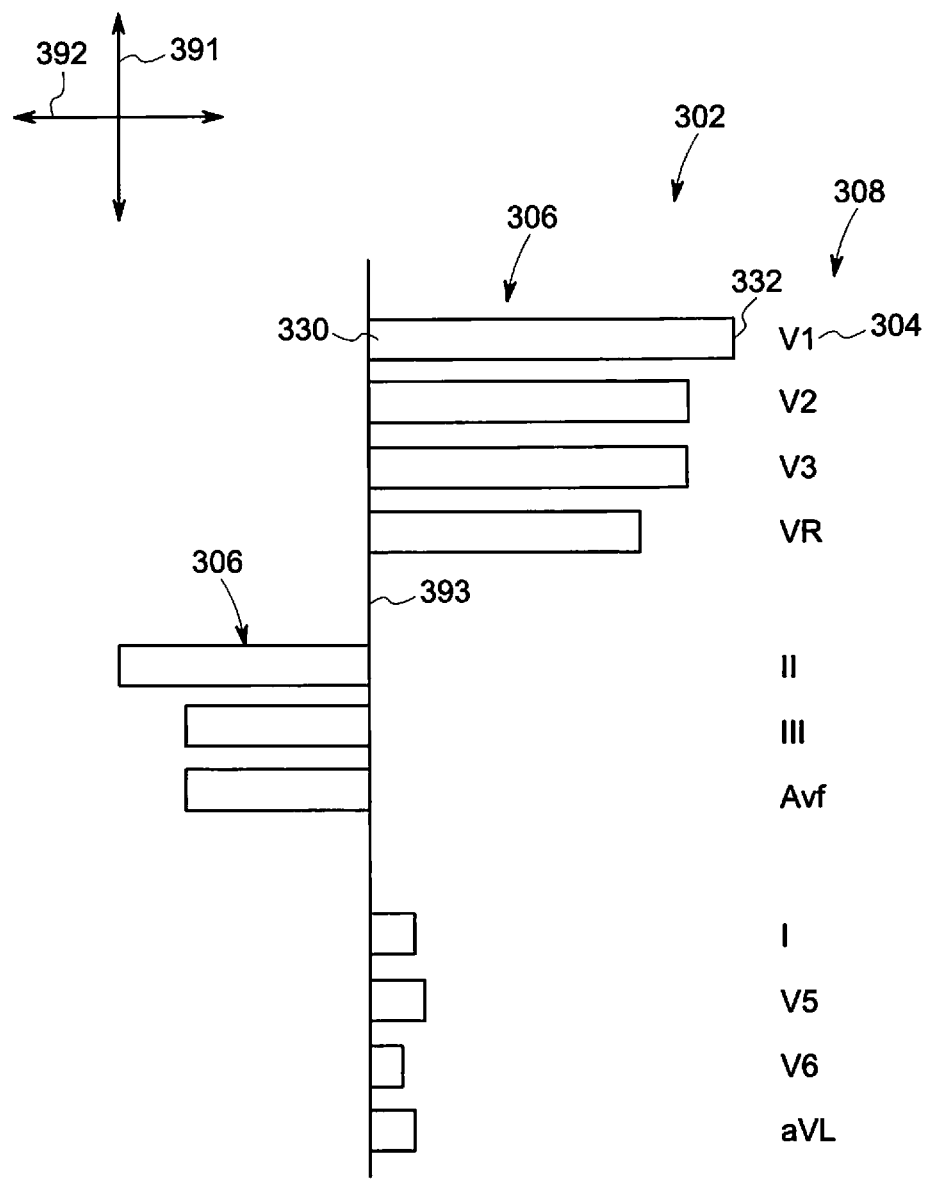
FIG. 5 illustrates a health chart that may be presented to a user of the system of FIG. 1 in accordance with an embodiment.

FIG. 5 illustrates a health chart 302 that may be presented to a user of the system of FIG. 1 in a monitoring window. The health chart 302 may include similar or identical features of the health chart 202 (FIG. 2). For example, the health chart 302 includes a plurality of indicators 304 that identify corresponding patient parameters. The plurality of indicators 304 form a column 308 that extends parallel to a first axis 391. Unlike the health chart 202, the column 308 is offset with respect to linear projections 306 of the health chart 302.

The linear projections 306 are aligned with respective indicators 304 and extend parallel to a second axis 392 that is perpendicular to the first axis 391. The linear projections 306 visually represent values of the patient parameters that correspond to the respective indicators 304. Each of the linear projections 306 has a proximal end 330 and a distal end 332. As shown, each of the proximal ends 330 are positioned on or immediately adjacent to a graph axis 393 that extends parallel to the first axis 391. The graph axis 393 is optional and may not appear on the health chart 302 in other embodiments. As described above, the distal ends 332 are configured to move toward or away from the graph axis 393 based on the physiological data. Although not shown, the health chart 302 may also display numerical values that numerically represent the value of the patient parameters.

Figure 6:
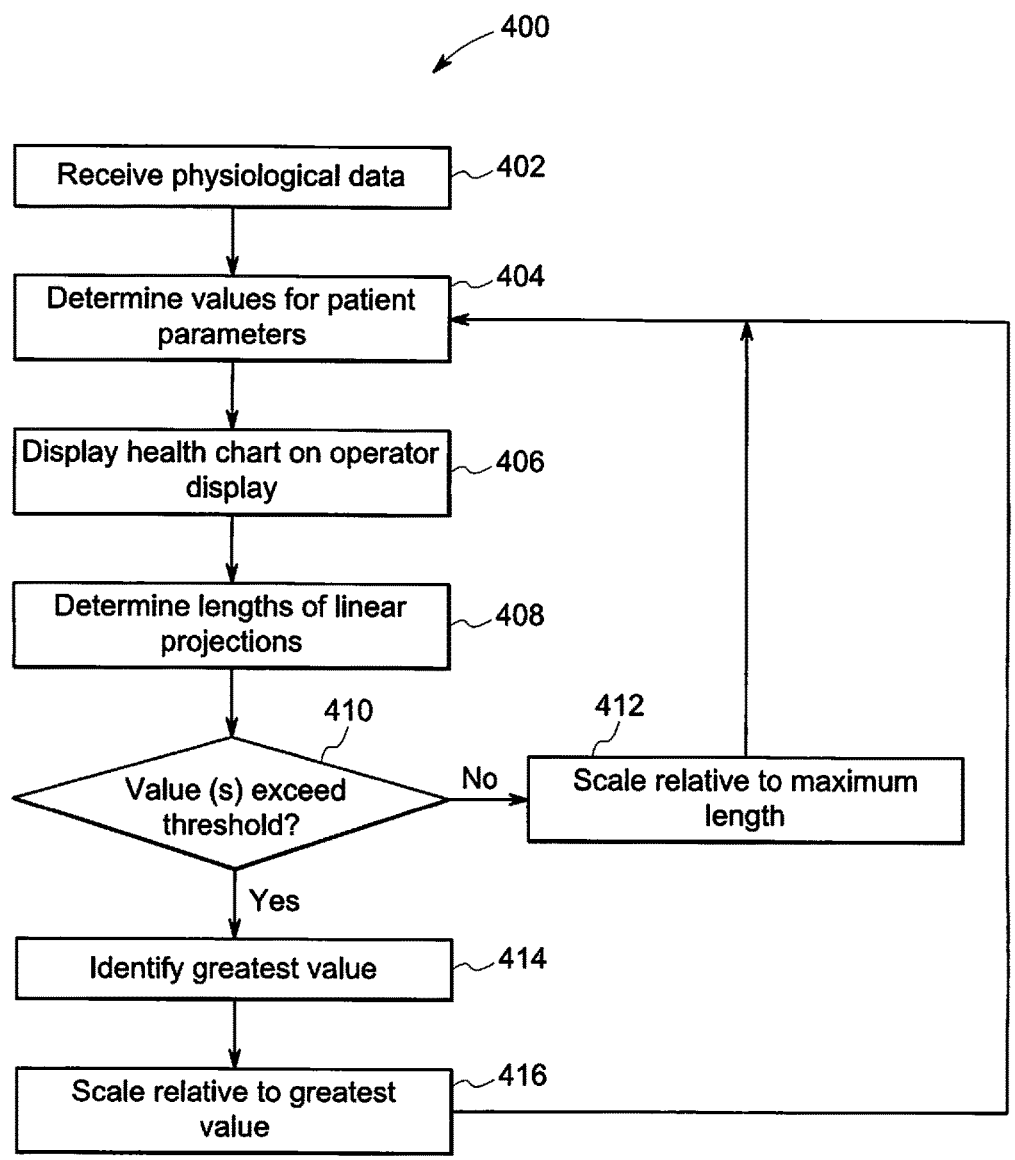
FIG. 6 illustrates a method of monitoring a patient in accordance with an embodiment.

FIG. 6 illustrates a method 400 of monitoring a patient in accordance with an embodiment. The method 400 includes receiving, at 402, physiological data from a patient. The method 400 also includes determining, at 404, values for a plurality of patient parameters. The values are a function of the physiological data. The method 400 also includes displaying or presenting, at 406, a health chart on an operator display. The health chart may be similar or identical to the health charts described herein and includes a plurality of indicators that identify corresponding patient parameters. The plurality of indicators form a column in the health chart that extends parallel to a first axis. The health chart also includes linear projections that are aligned with respective indicators and extend parallel to a second axis that is perpendicular to the first axis.

The method 400 also includes determining, at 408, corresponding lengths of the linear projections. The lengths of the linear projections represent the values of the patient parameters that correspond to the respective indicators. The corresponding lengths extend from proximal ends of the linear projections to distal ends of the linear projections. The distal ends move parallel to the second axis to change the length of the corresponding linear projection.

The determining, at 408, may include determining, at 410, whether the value of one or more patient parameters has exceeded a designated threshold. If the values have not exceeded the designated threshold, then the lengths of the linear projections are scaled relative to a maximum length at 412. If, however, one or more of the values have exceeded the designated threshold, then the method may identify, at 414, which value that exceeded the designated threshold is the greatest value. The method 400 may then scale the lengths of the linear projections based on the greatest value at 416. During a monitoring session, the method 400 may continue to receive physiological data, at 402, and repeatedly re-determine the values of the patient parameters, at 404, and the lengths of the linear projections, at 408. As such, the method 400 may provide for real-time monitoring of a plurality of patient parameters to facilitate determining a condition of a patient.

Figure 7:
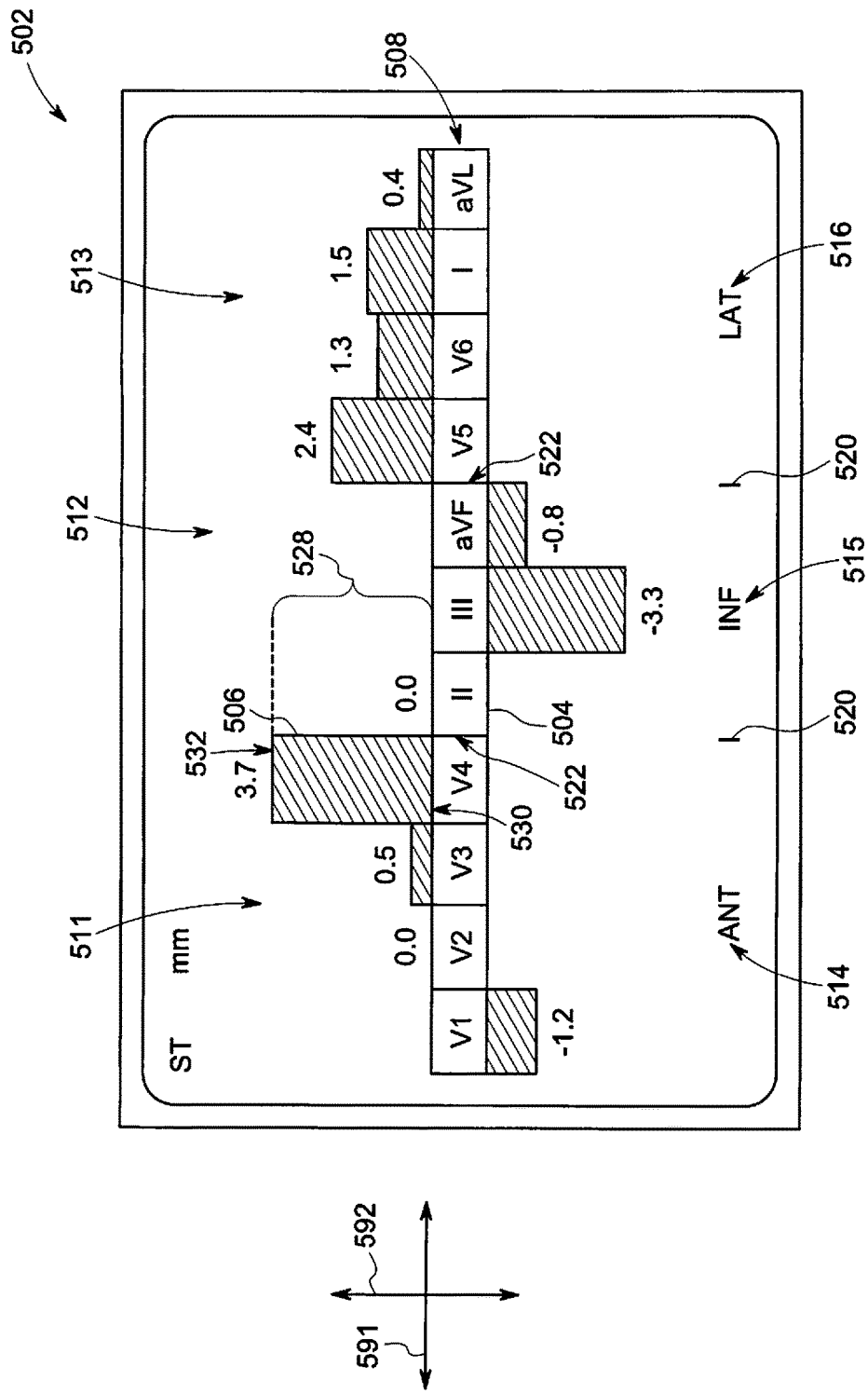
FIG. 7 illustrates a health chart that may be presented to a user of the system of FIG. 1 in accordance with an embodiment.

FIG. 7 illustrates a health chart 502 that may be presented to a user of the system of FIG. 1 in a monitoring window. The health chart 502 may include similar or identical features of the health chart 202 (FIG. 2) or the health chart 302 (FIG. 5). For example, the health chart 502 includes a plurality of indicators 504 that identify corresponding patient parameters. The plurality of indicators 504 form a column (or row) 508 that extends parallel to a first axis 591 and perpendicular to a second axis 592. Unlike the health chart 202, the column 508 extend horizontally across the health chart 502.

Each of the indicators 504 may be aligned with a linear projection 506. The linear projections 506 extend parallel to the second axis 592, which is perpendicular to the first axis 591. The linear projections 506 visually represent values of the patient parameters that correspond to the respective indicators 504. Each of the linear projections 506 has a proximal end 530 and a distal end 532. A length 528 of the corresponding linear projection 506 extends between the corresponding proximal and distal ends 530, 532. The length 528 is based on the physiological data obtained from the patient during a monitoring session. In the illustrated embodiment, each proximal end 530 is positioned adjacent to the indicator 504 that the corresponding linear projection 506 is associated with. Each distal end 532 is positioned away from the indicator 504 that the corresponding linear projection 506 is associated with. The distal end 532 is configured to move parallel to the second axis 592 to change the length 528 of the corresponding linear projection 506.

The indicators 504 and the corresponding linear projections 506 form a plurality of groups 511, 512, 513 in which each of the groups 511-513 includes multiple indicators 504 and the corresponding linear projections 506. In some embodiments, each of the groups 511-513 is visually differentiated from at least one other group. For example, the groups 511-513 have different labels 514-516, respectively. The indicators 504 of the group 511 are positioned above the label 514, the indicators 504 of the group 512 are positioned above the label 515, and the indicators 504 of the group 513 are positioned above the label 516. In other embodiments, the labels 514-516 may be positioned above the corresponding indicators 504. Moreover, a visual divider 520, which is illustrated as a vertical line in FIG. 7, is positioned to indicate where the groups 511 and 512 are separated. More specifically, a visual divider 520 is aligned with an interface 522 between the indicator 504 for the patient parameter V4 and the indicator 504 for the patient parameter II. Another visual divider 520 is aligned with an interface 522 between the indicator 504 for the patient parameter aVF and the indicator 504 for the patient parameter V5.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A monitoring system configured to monitor a condition of a patient, the system comprising:
 a plurality of sensors configured to operably couple to a patient to detect physiological data from the patient;
 an operator display configured to present a monitoring window that includes viewable information that is based on the physiological data of the patient; and
 a processor configured to execute programmed instructions stored in memory, wherein the processor, when executing the programmed instructions, performs the following operations:
 receives the physiological data from the patient;
 provides a health chart in the monitoring window that includes a plurality of indicators that identify corresponding patient parameters, the plurality of indicators forming a column that extends parallel to a first axis, the health chart also including linear projections that extend away from the column, the linear projections being aligned with respective indicators of the plurality of indicators and extending parallel to a second axis that is perpendicular to the first axis, wherein lengths of the linear projections are measured with respect to the respective indicators and represent values of the patient parameters that correspond to the respective indicators, the values being determined by the physiological data obtained from corresponding sensors; and
 determines the lengths of the linear projections based on the physiological data, the lengths extending from proximal ends of the linear projections to distal ends of the linear projections, the distal end moving parallel to the second axis to change the length of the corresponding linear projection.

2. The monitoring system in accordance with claim 1, wherein the indicators and corresponding linear projections form a plurality of groups in which each group includes multiple indicators and the corresponding linear projections.

3. The monitoring system in accordance with claim 2, wherein the groups include a first group of the indicators and a second group of the indicators, the first group corresponding to a first anatomical region of the heart, the second group corresponding to a second anatomical region of the heart.

4. The monitoring system in accordance with claim 2, wherein the groups are configured such that, during an alarm event, the values of the patient parameters of a first group are positive and the values of a second group are negative.

5. The monitoring system in accordance with claim 2, wherein each group is visually differentiated from at least one other group.

6. The monitoring system in accordance with claim 2, wherein the groups include a first group, a second group, and a third group, the patient parameters represented by the indicators of the first group relating to anterior walls of the heart, the patient parameters represented by the indicators of the second group relating to inferior walls of the heart, and the patient parameters represented by the indicators of the third group relating to lateral walls of the heart.

7. The monitoring system in accordance with claim 1, wherein the values of the patient parameters correspond to ST-segment deviations.

8. The monitoring system in accordance with claim 1, wherein the proximal ends are positioned adjacent to the corresponding indicators and the distal ends are configured to move toward or away from the corresponding indictors, wherein at least one of the linear projections is configured to extend in either direction away from the corresponding indicator based on the physiological data.

9. The monitoring system in accordance with claim 1, wherein the patient parameters correspond to at least one of electrical activity of the brain, heart rate, blood pressure, or auditory evoked potentials, the health chart presenting information to the user for monitoring a depth of anesthesia.

10. The monitoring system in accordance with claim 1, wherein the first axis is a vertical axis and the second axis is a horizontal axis, the indicators including symbols that identify the patient parameter, the symbols being oriented for reading along the horizontal axis.

11. The monitoring system in accordance with claim 1, wherein the processor repeatedly determines the corresponding lengths for real-time monitoring throughout a monitoring session.

12. The monitoring system in accordance with claim 1, wherein at least one of the linear projections is configured to extend in a first direction along the second axis and at least one other linear projection is configured to extend, at the same time, in an opposite second direction along the second axis.

13. The monitoring system in accordance with claim 1, wherein at least one of the linear projections is configured to extend away from the respective indicator in a first direction along the second axis and also, at a different time, extend away from the respective indicator in an opposite second direction along the second axis.

14. The monitoring system in accordance with claim 1, wherein the patient parameters correspond to electrical activity of the heart, the indicators and corresponding linear projections forming a plurality of groups in which each group includes multiple indicators and the corresponding linear projections, wherein at least two of the groups correspond to different anatomical regions of the heart, the at least two groups being visually differentiated from each other.

15. The monitoring system in accordance with claim 1, wherein the indicators form at least one group, the proximal ends of the linear projections of the at least one group having a common location along the second axis.

16. A monitoring system configured to monitor a condition of a patient, the system comprising:
a plurality of sensors configured to operably couple to a patient to detect physiological data from the patient;
an operator display configured to present a monitoring window that includes viewable information that is based on the physiological data of the patient; and
a processor configured to execute programmed instructions stored in memory, wherein the processor, when executing the programmed instructions, performs the following operations:
receives the physiological data from the patient;
provides a health chart in the monitoring window that includes a plurality of indicators that identify corresponding patient parameters, the plurality of indicators forming a column that extends parallel to a first axis, the health chart also including linear projections that extend away from the column, the linear projections being aligned with respective indicators of the plurality of indicators and extending parallel to a second axis that is perpendicular to the first axis, wherein lengths of the linear projections represent values of the patient parameters that correspond to the respective indicators, the values being determined by the physiological data obtained from corresponding sensors; and
determines the lengths of the linear projections based on the physiological data, the lengths extending from proximal ends of the linear projections to distal ends of the linear projections, at least one of the proximal end or the distal ends moving parallel to the second axis to change the length of the corresponding linear projection;
wherein, for at least one group of the indicators, the length of the linear projection of a respective indicator is independent of the length of other linear projections in the group, wherein, upon the value for one of the patient parameters obtaining a designated threshold, the lengths of the other linear projections are scaled relative to the length of the linear projection of the patient parameter that obtained the designated threshold.

17. A monitoring system configured to monitor a condition of a patient, the system comprising:
a plurality of sensors configured to operably couple to a patient to detect physiological data from the patient;
an operator display configured to present a monitoring window that includes viewable information that is based on the physiological data of the patient; and
a processor configured to execute programmed instructions stored in memory, wherein the processor, when executing the programmed instructions, performs the following operations:
receives the physiological data from the patient;
provides a health chart in the monitoring window that includes a plurality of indicators that identify corresponding patient parameters, the plurality of indicators forming a column that extends parallel to a first axis, the health chart also including linear projections that extend away from the column, the linear projections being aligned with respective indicators of the plurality of indicators and extending parallel to a second axis that is perpendicular to the first axis, wherein lengths of the linear projections represent values of the patient parameters that correspond to the respective indicators, the values being determined by the physiological data obtained from corresponding sensors; and
determines the lengths of the linear projections based on the physiological data, the lengths extending from proximal ends of the linear projections to distal ends of the linear projections, at least one of the proximal end or the distal ends moving parallel to the second axis to change the length of the corresponding linear projection;
wherein the indicators and corresponding linear projections form a plurality of groups in which each group includes multiple indicators and the corresponding linear projections, and wherein, during an alarm event, the linear projections of a first group extend designated distances away from the corresponding indicators in a first direction and the linear projections of a second group extend designated distances away from the corresponding indicators in a second direction that is opposite the first direction.

* * * * *